(12) United States Patent
Krill et al.

(10) Patent No.: US 6,316,661 B1
(45) Date of Patent: Nov. 13, 2001

(54) PROCESS FOR THE PRODUCTION OF 2,3,5-TRIMETHYLHYDROQUINONE DIESTERS

(75) Inventors: Steffen Krill, Speyer; Horst Weigel, Rodenbach; Klaus Huthmacher, Gelnhausen; Nongyuan Shi, Hainburg; Georg Markowz, Karlstein; Volker Hafner, Langenselbold, all of (DE)

(73) Assignee: Degussa Huls AG, Frankfurt am Main (DE)

( * ) Notice: Subject to any disclaimer, the term of this patent is extended or adjusted under 35 U.S.C. 154(b) by 0 days.

(21) Appl. No.: 09/493,065

(22) Filed: Jan. 28, 2000

(30) Foreign Application Priority Data

Jan. 28, 1999 (DE) .............................................. 199 03 269

(51) Int. Cl.$^7$ .................................................. C07C 69/00
(52) U.S. Cl. .............................................................. 560/144
(58) Field of Search ............................................. 560/144

(56) References Cited

U.S. PATENT DOCUMENTS 5,969,176   10/1999   Krill .

FOREIGN PATENT DOCUMENTS

| 198 05 690 A1 | 8/1999 | (DE) . |
| 0 850 910 A1 | 7/1998 | (EP) . |
| 0 916 642 A1 | 5/1999 | (EP) . |

*Primary Examiner*—Paul J. Killos
(74) *Attorney, Agent, or Firm*—Pillsbury Winthrop LLP

(57) ABSTRACT

A process for the production of 2,3,5-trimethylhydroquinone diesters by aromatization of 2,6,6-trimethyl-2-cyclohexene-1,4-dione (4-oxoisophorone, ketoisophorone, KIP) with an acylating agent and an acidic soluble or insoluble catalyst, which process may be operated alternatively continuously or discontinuously. The process includes the following steps: a) a carboxylic anhydride having a $C_1$ to $C_4$ alkyl residue is used as the acylating agent, b) after the reaction, a proportion of the resultant carboxylic acid is optionally removed by distillation, c) the reaction solution is cooled, d) the product which has crystallized out is separated and washed, and e) the filtrate is returned to step a).

10 Claims, No Drawings

PROCESS FOR THE PRODUCTION OF 2,3,5-TRIMETHYLHYDROQUINONE DIESTERS

CROSS-REFERENCE TO RELATED APPLICATION

This application is based on German Application DE 199 03 269.6, filed Jan. 28, 1999, which disclosure is incorporated herein by reference.

FIELD OF THE INVENTION

This invention relates to a process for the production of 2,3,5-trimethylhydroquinone diesters by aromatization of 2,6,6-trimethyl-2-cyclohexene-1,4-dione (4-oxoisophorone, ketoisophorone, KIP) with an acylating agent and an acidic soluble or insoluble catalyst, which process may be operated either continuously or discontinuously or in a combination of these modes.

BACKGROUND OF THE INVENTION 2,3,5-Trimethylhydroquinone diesters are not only valuable intermediates in the synthesis of vitamin E and other pharmaceutically active chromane compounds, but are also widely used as antioxidants.

The formation of 2,3,5-trimethylhydroquinone diesters from KIP in the presence of a strongly acidic catalyst and an acylating agent such as carboxylic anhydrides, acyl halides or enol esters is known and has been described in several patents (for example DE 26 46 172 C2, EP 808 815 A2 and EP 0 850 910 A1).

It is furthermore known that while this aromatization may indeed be performed at up to 100% conversion, primarily depending upon the catalyst, selectivity is between 80 and 95%. The secondary product which is mainly formed is the isomeric 3,4,5-trimethylpyrocatechol diester. This secondary reaction, which always occurs, is described in EP 0 850 912 A1.

Isolating the 2,3,5-trimethylhydroquinone diester from the reaction solution and purifying it is complex and entails considerable losses. In examples using dissolved catalysts, the mixture of 2,3,5-trimethylhydroquinone diester and the 3,4,5-trimethylpyrocatechol diester is precipitated by addition of water or basic aqueous solutions and purified by recrystallization from organic solvents. Recovering the catalyst from the filtrate is complex and the yield is greatly reduced on recrystallization. The acylating agent, which is introduced into the aromatization reaction in excess, hydrolyzes and is unusable for subsequent reactions.

When undissolved catalysts are used, such as strongly acidic ion exchangers or H-Y zeolites, separation and reuse of the catalyst is simple, but the isolation and high-loss purification of the 2,3,5-trimethylhydroquinone diester are no different from the reaction solutions using dissolved catalysts.

Due to the low isolation yield and the large quantities of waste, as an industrial production process, this method is associated with serious economic and environmental disadvantages.

SUMMARY OF THE INVENTION

The object of the invention is to provide a process by means of which 2,3,5-trimethylhydroquinone diesters may be produced with solid or dissolved catalysts with minimal amounts of waste in a continuous or discontinuous mode of operation or in a combination of these modes.

The present invention provides a process for the production of 2,3,5-trimethylhydroquinone diesters by catalytic reaction of ketoisophorone (KIP) with an acylating agent, characterized in that, a) a carboxylic anhydride having a $C_1$ to $C_4$ alkyl residue is used as the acylating agent;

b) after the acylating reaction a proportion of the resultant carboxylic acid is optionally removed by distillation c) the reaction solution is cooled to a temperature of $-10°$ to $35°$ C., preferably of 0 to $30°$ C.;

d) the product which has crystallized out is separated and washed; and e) the filtrate is returned to step a), optionally after removing a proportion of the resultant carboxylic acid by distillation and optionally after discharging a proportion of the filtrate.

The reaction of KIP with a carboxylic anhydride in the presence of a strongly acidic catalyst results in the formation of 2,3,5-trimethylhydroquinone diester, the isomeric trimethylpyrocatechol diester and carboxylic acid. 2 Mol of carboxylic acid are formed per mol of reacted KIP.

It has been found that the carboxylic acid formed during the reaction is well suited to separating the 2,3,5-trimethylhydroquinone diester and 3,4,5-trimethylpyrocatechol diester. The two aromatic compounds may be separated by simple crystallization from carboxylic acids, preferably acetic acid. Despite the similarity of the molecules, no mixed crystals are formed.

After the reaction is complete, the reaction solution is cooled and 2,3,5-trimethylhydroquinone diester is crystallized. After the crystals have been separated and the optionally used solid catalyst has previously been removed by filtration, a filtrate remains, corresponding to the proportion of the 2,3,5-trimethylhydroquinone diester which has not been filtered out, the 3,4,5-trimethylpyrocatechol diester formed as secondary product, the catalyst optionally used in dissolved form together with the carboxylic anhydride introduced in excess. This filtrate, denoted the recycle solution, comprising a saturated product solution with all secondary products, unreacted educts and optionally the catalyst, is completely recycled, wherein no new catalyst need be added in the case of a homogeneous reaction. The acylating agent may now be introduced in a stoichiometric quantity as the excess required for complete conversion of KIP is present in the recycled filtrate.

On each recirculation, the volume of the solution increases by the formation of 2 mol of carboxylic acid per mol of converted KIP, wherein due to the good solubilizing power only a proportion of the diester formed crystallizes out. A proportion of the carboxylic acid is accordingly preferably removed by distillation, so maintaining the quantity of the recycle solution at a constant volume. The distillation step may be performed alternatively before or after separation of the crystals.

The trimethylpyrocatechol diester and, to some slight extent, also other secondary products, accumulate in the recycle solution. The concentration of trimethylhydroquinone diester may rise to close to the saturation concentration without disadvantage. This saturation concentration value is obtained from the solubility curve and crystallization temperature. In the case of the diacetate, at a crystallization temperature of $20°$ C., the concentration of trimethylpyrocatechol diacetate in the recycle solution may rise to up to 20 wt. %, wherein the isolated product remains pure. The content of secondary products in the solution may be maintained at a tolerable level by discharging a sub-stream of the recycle solution. The quantities of catalyst and acylating agent contained therein are made up by appropriate additions to the cycle.

The process according to the invention for the production of trimethylhydroquinone diesters generates another advantage. As the concentration of trimethylpyrocatechol diacetate in the recycle solution rises, selectivity for the formation of further quantities of this secondary product decreases. When the concentration of the trimethylpyrocatechol diacetate rises from 0 to 15 wt % in the recycle solution, selectivity for the formation of further quantities thereof is virtually halved.

The crystals of the desired product are washed using the corresponding carboxylic acid, a saturated product solution in the carboxylic acid or also using an inert solvent such as, for example, hydrocarbons or ethers, which solvent is recovered by distillation.

In the process according to the invention, all the process steps may optionally be designed such that the operation proceeds continuously, partially continuously, batchwise or in a combination thereof.

The process consists of the sub-steps: chemical reaction (I), distillation (II), crystallization (III) and separation of solids (IV). Sub-steps II and III may be combined into a single step. The sequence may also be selected such that, after the chemical reaction (I), crystallization (III) and separation of solids (IV) proceed first and then distillation (II).

The educts, ketoisophorone and an acylating agent, preferably acetic anhydride, and the recycle solution are introduced into the reactor for the chemical reaction. The type of reactor is influenced by the properties of the catalyst used and may, for example, comprise a reactor having a fixed bed, a simple tank or a mixing vessel with a subsequent holding section. The quantity of recycle solution may be within the range from 4 to 20 kg, preferably from 5 to 10 kg, per kg of introduced ketoisophorone and should be calculated such that the crystal slurry is free-flowing after crystallization.

The required holding time depends upon the nature and quantity of the catalyst used and the selected temperature, wherein the conditions are preferably selected such that a holding time of 1 to 3 hours is sufficient. Since the excess educts present in the filtrate are recycled in the process according to the invention, ketoisophorone conversion may be below 100%.

The carboxylic acid, acetic acid in the case of the preferred use of acetic anhydride, is conveniently removed by distillation continuously or discontinuously via a column, the separation efficiency of which is sufficient for the carboxylic anhydride to remain in the bottoms. The quantity of distillate removed is such that the volume of the recycle solution remains constant. Propionic anhydride may also be used.

When the reaction solution cools, the trimethylhydroquinone diester crystallizes out, while the trimethylpyrocatechol diester remains in solution. The temperature for the crystallization operation may be between −10° and +35° C., wherein the range from 0 to 30° C. is preferred. Crystallization may be performed in a single stage or in multiple stages. The crystallization process step is performed in a known manner continuously or discontinuously, wherein it is advantageous to add seed crystals due to the tendency of the solution to become supersaturated.

Separation of solids proceeds continuously or discontinuously using conventional units, wherein care must be taken to ensure the absence of moisture, so that the excess acylating agent present in the filtrate is not hydrolyzed. A washing operation is required in order to displace any adhering mother liquor. The washing liquid used may, for example, comprise a proportion of the carboxylic acid removed by distillation, an inert organic solvent such as petroleum benzene or advantageously a solution of trimethylhydroquinone diester in the carboxylic acid.

The filtrate is recycled together with the excess educts and optionally with the dissolved catalyst and secondary products. The content of trimethylpyrocatechol diester in the filtrate may rise to up to 20 wt. % without disadvantage. In order to obtain a consistently clean product, according to the invention a proportion of the filtrate is discharged once the filtrate has been recycled several times. The quantity so discharged is that in which the quantity of pyrocatechol diester newly formed in a cycle is dissolved.

DETAILED DESCRIPTION OF THE PREFERRED EMBODIMENTS

The following Example is intended to illustrate the process according to the invention, but is not intended to be restrictive.

EXAMPLE 1

The reaction vessel consists of a temperature-controlled jacketed vessel equipped with a stirrer, overflow and inlets for the recycle solution, KIP and acetic anhydride. 76 g of KIP, 110 g of acetic anhydride and 500 g of recycle solution are pumped in per hour. The recycle solution contains 31% trimethylhydroquinone diacetate, 17% trimethylpyrocatechol diacetate, 0.8% trifluoromethanesulfonic acid, 38% acetic acid and 10% acetic anhydride. The vessel is temperature-controlled in such a manner that the internal temperature is 50 to 55° C. The homogeneous overflow solution is passed through a tube temperature-controlled to 55° C. as post-reactor. The total volume of the reaction vessel and post-reactor is 1.4 L.

The reaction solution is introduced into a distillation apparatus and 58 g/h of acetic acid are removed by distillation at 30 mbar.

The distillation bottoms are introduced into the crystallization and cooled to 20° C. while being stirred. At 5 hour intervals, the resultant suspension is filtered and the adhering solution is displaced by washing with 220 g of a saturated solution of trimethylhydroquinone diacetate in acetic acid. 4% of the filtrate is discharged. The remaining filtrate is reintroduced into the reaction vessel together with 1.3 g of fresh catalyst.

The solids are dried under a vacuum. The resultant trimethylhydroquinone diacetate has a purity of >98% and the isolation yield is 88%, relative to introduced ketoisophorone.

What is claimed is:
1. A process for the production of 2,3,5-trimethylhydroquinone diesters by catalytic reaction of ketoisophorone (KIP) with an acylating agent, comprising:
   a) catalytically reacting ketoisophorone with an acylating agent in a reaction solution, the acylating agent comprising a carboxylic anhydride having a $C_1$ to $C_4$ alkyl residue;
   b) optionally removing a proportion of resultant carboxylic acid by distillation;
   c) cooling resultant solution to a temperature of −10° to 35° C.;
   d) separating and washing product which has crystallized out; and e) optionally removing a proportion of resultant carboxylic acid by distillation;

f) optionally discharging the proportion of filtrate;

g) returning resulting filtrate to step a) as recycle solution.

2. The process according to claim 1, wherein, when a solid catalyst is used, the catalyst is separated before step c).

3. The process according to claim 1, wherein the acylating agent is acetic anhydride or propionic anhydride.

4. The process according to claim 1, wherein the reaction includes recycling the filtrate.

5. The process according to claim 4, wherein a proportion of the carboxylic acid is removed by distillation and amount of the recycle solution is maintained at a constant value.

6. The process according to claim 1, wherein concentration of trimethylpyrocatechol in the reaction solution is maintained below the solubility limit at the crystallization temperature by discharging a proportion of the recycle solution.

7. The process according to claim 1, wherein the resultant solution in step c) is cooled to a temperature of 0 to 30° C.

8. The process according to claim 4, wherein product is crystallized out at 0 to 30° C. in step c).

9. The process according to claim 1, wherein amount of recycle solution is calculated such that a crystallization slurry is free-flowing after crystallization.

10. The process according to claim 1, wherein the process is performed continuously, partially continuously or batchwise.

* * * * *